Feb. 12, 1974 J. ANDREW Plant Pat. 3,471
ALMOND TREE
Filed Oct 20, 1971
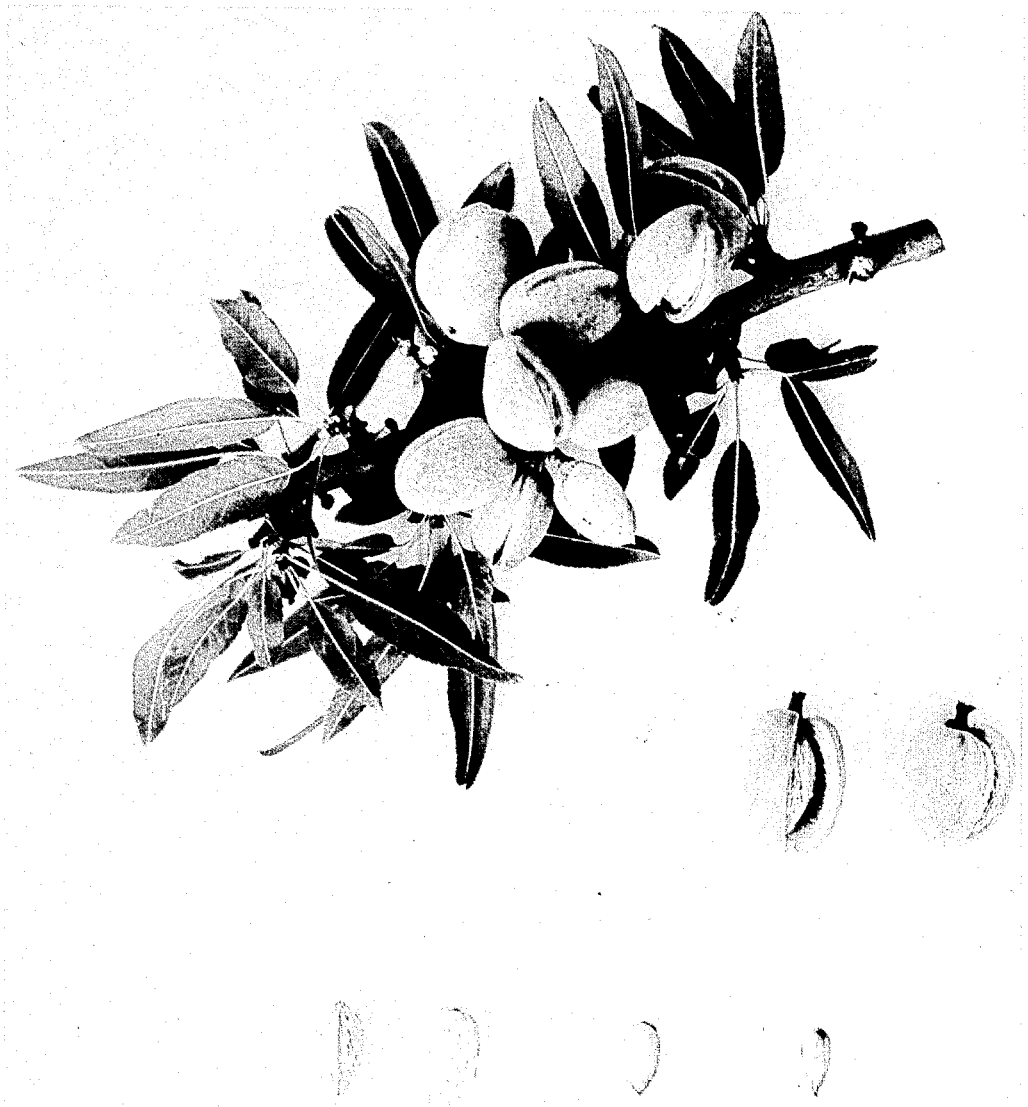

United States Patent Office

Plant Pat. 3,471
Patented Feb. 12, 1974

3,471

ALMOND TREE

John Andrew, 15760 W. 1st Ave.,
Delhi, Calif. 95315

Filed Oct. 20, 1971, Ser. No. 191,044
Int. Cl. A01h 5/03
U.S. Cl. Plt.—30 1 Claim

ABSTRACT OF THE DISCLOSURE

An almond tree which is of medium size, dense, vigorous, medium in branching habit, abundant of foliage with medium size, lanceolate, acutely pointed leaves, heavy to very heavy in pink bloom approximately with Nonpareil (unpatented), and a regular and very heavy producer of small, completely closed nuts well distributed on the tree; the nuts hanging well on the tree, harvesting easily approximately with Nonpareil, and being easy to hull.

Origin of the variety.—The present variety of almond tree was discovered by me growing, as an apparently chance seedling, in an almond orchard, of which I am presently an owner, located near Delhi, Merced County, Calif. Subsequent to recognition by me of the distinctive characteristics—which will herein later appear—of the original tree, I propagated the variety looking in the direction of ultimate commercial planting thereof.

Asexual reproduction of the variety.—The present variety of almond tree was asexually reproduced by me, with professional assistance, by bud grafting on mature almond trees in the aforesaid orchard, and, in maturity, such reproductions ran true to the original tree in all respects.

Summary of the variety.—The present variety of almond tree is, characteristically, of medium size, dense, vigorous, medium in branching habit, abundant of foliage with medium size, lanceolate, acutely pointed leaves, heavy to very heavy in pink bloom approximately with Nonpareil, and a regular and very heavy producer of small, completely closed nuts well distributed on the tree; the nuts hanging well on the tree, harvesting easily approximately with Nonpareil, and being easy to hull.

The present variety of almond tree is additionally characterized by its ability to serve as a pollinator for the Nonpareil, Mission (unpatented), Merced (U.S. Plant Pat. No. 1,730), and Thompson (U.S. Plant Pat. No. 1,526). Further, the present variety cross pollinates with the Nonpareil and Mission.

The present variety of almond tree is also characterized by an apparent substantial resistance to mites, red spider, shot-hole fungus, and brown rot. Another advantage is a substantial resistance—because of the complete closure of the nuts—to penetration of the shell by insects and worms, and by moisture which otherwise may produce internal mold.

Brief description of the drawing.—The drawing is an illustration, by photographic reproduction in color, of a twig with leaves and nuts, detached nuts in hull, nuts out of hull, and meats.

Description of the variety.—The botanical details of this new and distinct variety of almond tree—with color definitions (except those in common color terms) referenced to Maerz and Paul Dictionary of Color—are as follows:

Tree:
- *Size.*—Medium.
- *Density.*—Dense.
- *Vigor.*—Vigorous.

Trunk:
- *Form.*—Stocky.
- *Texture.*—Shaggy.

Branches:
- *Form.*—Medium.
- *Texture.*—Medium.
- *Lenticels.*—Few, small.
- *Branching habit.*—Medium.
- *Color.*—New wood—green. Mature wood—brown.

Foliage:
- *Quantity.*—Abundant.

Leaves:
- *Size.*—Medium. Average length—81 mm. Average width—18 mm.
- *Shape.*—Lanceolate, acutely pointed.
- *Thickness.*—Medium.
- *Texture.*—Smooth.
- *Margin.*—Coarsely serrate.
- *Petiole.*—Short. Slender.
- *Glands.*—Average number—2 to 3, opposite, small, globose, green, positioned on petiole adjacent blade.
- *Stipules.*—None.
- *Color.*—Top side—Medium green (23–J–8), under side—Lighter green (22–K–7).

Bloom:
- *Amount of bloom.*—Heavy to very heavy.
- *Color.*—Pink.
- *Blooming period.*—Medium—February 22–27. Approximately with Nonpareil.

Crop:
- *Bearing.*—Regular bearer.
- *Productivity.*—Very heavy.
- *Distribution of nuts on tree.*—Well distributed.
- *Harvest period.*—About September 15—approximately with Nonpareil.
- *Tenacity.*—Hangs well on tree. Easy to harvest. Easy to hull.

Hull:
- *Outer surface.*—Smooth.
- *Form.*—Regular.
- *Thickness.*—Thick.
- *Flesh.*—Fleshy.
- *Suture.*—Ridged.
- *Color.*—Light green (21–I–5), with a silvery sheen.
- *Dehiscence.*—Opens freely.
- *Splitting.*—Along suture.

Nut:
- *Size.*—Small. Average length—30 mm. Average width—17 mm. Average thickness—15 mm.
- *Form.*—Length/width, ovate. Width/thickness, plump.
- *Shell.*—Soft, thick, smooth. Outer shell: Crumbling; Adheres to hull. Inner shell: Soft; well sealed.
- *Color.*—Straw (11–I–4).
- *Pits.*—Large, numerous, deep, round.
- *Base.*—Square.
- *Stem scar.*—Large, acute.
- *Apex.*—Obtuse, sharp, blunt, prolonged at tip.
- *Wing.*—Narrow, thin, tapered toward base.
- *Inner surface.*—Light colored.
- *Ventral streak.*—Dark, broad, long, point acute.
- *Percentage of kernel to nut.*—52.9%.

Kernel:
- *Size.*—Small. Average length—22 mm. Average width—12 mm. Average thickness—9 mm.
- *Form.*—Length/width: Ovate. Width/thickness: plump.
- *Base.*—Dorsally oblique.
- *Stem scar.*—Large, obtuse.
- *Apex.*—Obtuse, sharp, blunt, prolonged at tip.
- *Surface.*—Wrinkled, furrowed.

*Pellicle.*—Thin.
*Pubescence.*—Smooth, veined.
*Color.*—Medium light brown (14–J–11).
*Number of doubles.*—Few.
*Defective kernels.*—Very few.
*Flavor.*—Dry, sweet.
*Quality.*—Very good.

*Resistance to insects and diseases*: Apparent substantial resistance to mites, shot-hole fungus, red spider, and brown rot.

The almond tree and its nuts herein described may vary in slight detail due to clamatic and soil conditions under which the variety may be grown; the present description being of the variety as grown in the Central Valley of California.

I claim:

1. A new and distinct variety of almond tree, substantially as shown and described, which is of medium size, dense, vigorous, medium in branching habit, abundant of foliage with medium size, lanceolate, acutely pointed leaves, heavy to very heavy in pink bloom approximately with Nonpareil, and a regular and very heavy producer of small, completely closed nuts well distributed on the tree; the nuts hanging well on the tree, harvesting easily approximately with Nonpareil, and being easy to hull.

No references cited.

ROBERT E. BAGWILL, Primary Examiner